(12) United States Patent
Honda et al.

(10) Patent No.: US 9,327,140 B2
(45) Date of Patent: May 3, 2016

(54) BEAM DATA PROCESSING APPARATUS AND PARTICLE BEAM THERAPY SYSTEM

(75) Inventors: Taizo Honda, Tokyo (JP); Yuichi Yamamoto, Tokyo (JP); Yuehu Pu, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/115,028

(22) PCT Filed: Aug. 23, 2011

(86) PCT No.: PCT/JP2011/068927
§ 371 (c)(1),
(2), (4) Date: Oct. 31, 2013

(87) PCT Pub. No.: WO2013/027263
PCT Pub. Date: Feb. 28, 2013

(65) Prior Publication Data
US 2014/0061498 A1    Mar. 6, 2014

(51) Int. Cl.
*G01K 1/08* (2006.01)
*A61N 5/10* (2006.01)
*G21K 5/04* (2006.01)

(52) U.S. Cl.
CPC ............ *A61N 5/1048* (2013.01); *A61N 5/1043* (2013.01); *A61N 5/1075* (2013.01);
(Continued)

(58) Field of Classification Search
CPC ............. A61N 5/06; H05H 3/00; H05H 5/00; H05H 7/02; H05H 13/10; H05H 2277/10; G21G 4/08
USPC ................. 250/397, 396 R, 400, 492.1, 492.3
See application file for complete search history.

(56) References Cited

U.S. PATENT DOCUMENTS 5,017,789 A * 5/1991 Young et al. ............ 250/396 ML
7,372,386 B1 * 5/2008 Maloberti ........... H03M 1/0626
341/137

(Continued)

FOREIGN PATENT DOCUMENTS

JP    63-31643 A    2/1988
JP    03-103794 A    4/1991

(Continued)

OTHER PUBLICATIONS

International Search Report (PCT/ISA/210) mailed on Nov. 1, 2011, by the Japanese Patent Office as the International Searching Authority for International Application No. PCT/JP2011/068927.
(Continued)

*Primary Examiner* — Nicole Ippolito
*Assistant Examiner* — Jason McCormack
(74) *Attorney, Agent, or Firm* — Buchanan Ingersoll & Rooney PC (57) ABSTRACT

A beam data processing apparatus has a plurality of channel data conversion units that convert a plurality of analogue signals outputted from a position monitor into digital signals, a position size processing unit that calculates a beam position, based on voltage information items obtained through processing by the plurality of channel data conversion units, an abnormality determination processing unit that determines the beam position and generates a position abnormality signal, and an integrated control unit that controls the plurality of channel data conversion units in such a way that while a beam is stopped at an irradiation spot, digital signal conversion processing is implemented two or more times; the channel data conversion unit has a plurality of A/D converters, a demultiplexer that distributes analogue signals, and a multiplexer that switches respective digital signals processed by the A/D converters so as to output them to the position size processing unit.

6 Claims, 7 Drawing Sheets

(52) U.S. Cl.
CPC ....... *A61N5/1077* (2013.01); *A61N 2005/1074* (2013.01); *A61N 2005/1087* (2013.01); *G21K 5/04* (2013.01)

(56) References Cited

U.S. PATENT DOCUMENTS

| | | | |
|---|---|---|---|
| 2007/0176125 A1* | 8/2007 | Natori et al. ............... | 250/493.1 |
| 2008/0084346 A1* | 4/2008 | Minichshofer et al. ....... | 342/118 |
| 2010/0148087 A1* | 6/2010 | Doering et al. ........... | 250/396 R |
| 2010/0243911 A1 | 9/2010 | Fujii et al. | |
| 2011/0220807 A1* | 9/2011 | Inoue .................... | A61N 5/1042 250/393 |
| 2012/0305796 A1 | 12/2012 | Iseki et al. | |

FOREIGN PATENT DOCUMENTS

| | | |
|---|---|---|
| JP | 03-109648 A | 5/1991 |
| JP | 11-347023 A | 12/1999 |
| JP | 2003-263420 A | 9/2003 |
| JP | 2003-294844 A | 10/2003 |
| JP | 2009-050468 A | 3/2009 |
| JP | 2010-060523 A | 3/2010 |
| JP | 2010-253250 A | 11/2010 |
| WO | WO 2011/099449 A1 | 8/2011 |

OTHER PUBLICATIONS

European Search Report Issued Feb. 17, 2015 in corresponding EP Application No. 11871175.3 filed on Aug. 23, 2011 (6 pages).
Chinese Office Action issued by the State Intellectual Property Office of the People's Republic of China on Jul. 31, 2015 in corresponding Chinese Application No. 201180072970.7, with full English translation (12 pages).

\* cited by examiner

BEAM DATA PROCESSING APPARATUS AND PARTICLE BEAM THERAPY SYSTEM

TECHNICAL FIELD

The present invention relates to a particle beam therapy system utilized in the medical field and R&Ds and particularly to data processing of the position and the size of a particle beam in a particle beam therapy system of a scanning type such as a spot-scanning type or a raster-scanning type.

BACKGROUND ART

In general, a particle beam therapy system is provided with a beam generation apparatus that generates a charged particle beam, an accelerator that is connected with the beam generation apparatus and accelerates a generated charged particle beam, a beam transport system that transports a charged particle beam that is accelerated by the accelerator so as to gain predetermined energy and then emitted, and a particle beam irradiation apparatus, disposed at the downstream side of the beam transport system, for irradiating a charged particle beam onto an irradiation subject. Particle beam irradiation apparatuses are roughly divided into apparatuses utilizing a broad irradiation method in which a charged particle beam is enlarged in a dispersion manner by a scatterer, and the shape of the enlarged charged particle beam is made to coincide with the shape of an irradiation subject in order to form an irradiation field; and apparatuses utilizing a scanning irradiation method (the spot-scanning method, the raster-scanning method, and the like) in which an irradiation field is formed by performing scanning with a thin, pencil-like beam in such a way that the scanning area coincides with the shape of an irradiation subject.

In the broad irradiation method, an irradiation field that coincides with the shape of a diseased site is formed by use of a collimator or a bolus. The broad irradiation method is a most universally utilized and superior irradiation method where an irradiation field that coincides with the shape of a diseased site is formed so as to prevent unnecessary irradiation onto a normal tissue. However, it is required to create a bolus for each patient or to change the shape of a collimator in accordance with a diseased site.

In contrast, the scanning irradiation method is a high-flexibility irradiation method where, for example, neither collimator nor bolus is required. However, because these components for preventing irradiation onto not a diseased site but a normal tissue are not utilized, there is required a positional accuracy of beam irradiation that is the same as or higher than that of the broad irradiation method.

Patent Document 1 discloses a beam position monitor, for a particle beam therapy system, that has a purpose of solving the problem that in a raster-scanning irradiation method in which when the irradiation position is changed, the charged particle beam is not stopped, the accuracy of beam position measurement is deteriorated mainly by the fact that the electric charges collected during the scanning of the charged particle beam and the electric charges collected when the scanning has been completed cannot accurately be distinguished from each other. The beam position monitor according to Patent Document 1 is provided with a collection electrode (corresponding to a sensor unit of the position monitor) for collecting collection charges produced by ionization of the charged particle beam, and a signal processing circuit that performs a beam position calculation for determining the beam position by utilizing collection charges. The signal processing circuit is provided with an I/V converter that generates a voltage signal obtained by I/V-converting the current output from the collection electrode; a digital signal generation circuit that generates a digital signal related to the collection charges when the voltage signal is inputted thereto; a timing signal transmission/reception unit that receives a signal, as a timing signal, that is generated at a time when the charged particle beam, which is scanned from a scanning-stop irradiation point (corresponding to an irradiation spot in a spot scanning irradiation method) to the next scanning-stop irradiation point, is in the non-scanning state (in which the charged particle beam is stopped at the scanning-stop irradiation point); and a beam position calculation unit that calculates a beam position by use of a digital signal related to collection charges when a digital signal, related to the collection charges, generated by the digital signal generation circuit at the timing when the timing signal transmission/reception unit receives the timing signal, is inputted thereto.

PRIOR ART REFERENCE

Patent Document

[Patent Document 1] Japanese Patent Application Laid-Open No. 2010-60523 (Paragraphs 0008 through 0011, FIG. 7)

DISCLOSURE OF THE INVENTION

Problems to be Solved by the Invention

In the invention disclosed in Patent document 1, the irradiation position at a time when the scanning of a charged particle beam is stopped at a scanning-stop irradiation point set on a treatment subject and then the charged particle beam is irradiated can be obtained only once at the timing of a signal to be generated in the non-scanning state where no charged particle beam is scanned; however, because a plurality of irradiation position calculations are not implemented during irradiation at the scanning-stop irradiation point, there is posed a problem that even when the charged particle beam moves and falls out of the tolerance range, that irradiation position cannot be detected. Even in the case where a particle beam therapy system provided with the beam position monitor according to Patent Document 1 has a function of stopping the irradiation of a charged particle beam when the irradiation position is abnormal, no abnormality detection signal can be generated for an abnormality caused after the timing of data collection at a single scanning-stop irradiation point; therefore, there is posed a problem that the irradiation of the charged particle beam cannot immediately be stopped.

The present invention has been implemented in order to solve the foregoing problems; the objective thereof is to obtain a beam data processing apparatus that detects the irradiation position of a charged particle beam even when in an irradiation spot, a position abnormality of the charged particle beam is caused during the irradiation of the charged particle beam and that can generate an abnormality detection signal for indicating the position abnormality of the charged particle beam.

Means for Solving the Problems

A beam data processing apparatus according to the present invention is provided with a plurality of channel data conversion units that perform AD conversion processing in which each of the plurality of analogue signals outputted from a position monitor that detects with a plurality of detection channels the passing position of a charged particle beam is converted into a digital signal; a position size processing unit that calculates a beam position, which is the passing position of the charged particle beam in the position monitor, based on voltage information items obtained through processing by the plurality of channel data conversion units; an abnormality determination processing unit that determines whether or not the beam position is within a tolerance range, based on a desired position of the charged particle beam and a position allowable value, and that generates a position abnormality signal when determining that the beam position is not within the tolerance range; and an integrated control unit that controls the plurality of channel data conversion units in such a way that while the charged particle beam is stopped at an irradiation spot, digital signal conversion processing is implemented two or more times. The channel data conversion unit has a plurality of A/D converters, a demultiplexer that distributes the respective analogue signals to the A/D converters at different timings, and a multiplexer that switches the respective digital signals processed by the A/D converters at different timings so as to output them to the position size processing unit.

Advantage of the Invention

A beam data processing apparatus according to the present invention is provided with two or more A/D converters for each detection channel of a position monitor, and the two or more A/D converters are operated at different timings while a charged particle bean is stopped at an irradiation spot; therefore, it is made possible to detect the irradiation position of the charged particle beam even in the case where while the charged particle beam is irradiated at an irradiation spot, a position abnormality of the charged particle beam is caused and to generate an abnormality detection signal for indicating the position abnormality of the charged particle beam.

BEST MODE FOR CARRYING OUT THE INVENTION

Embodiment 1

Figure 1:
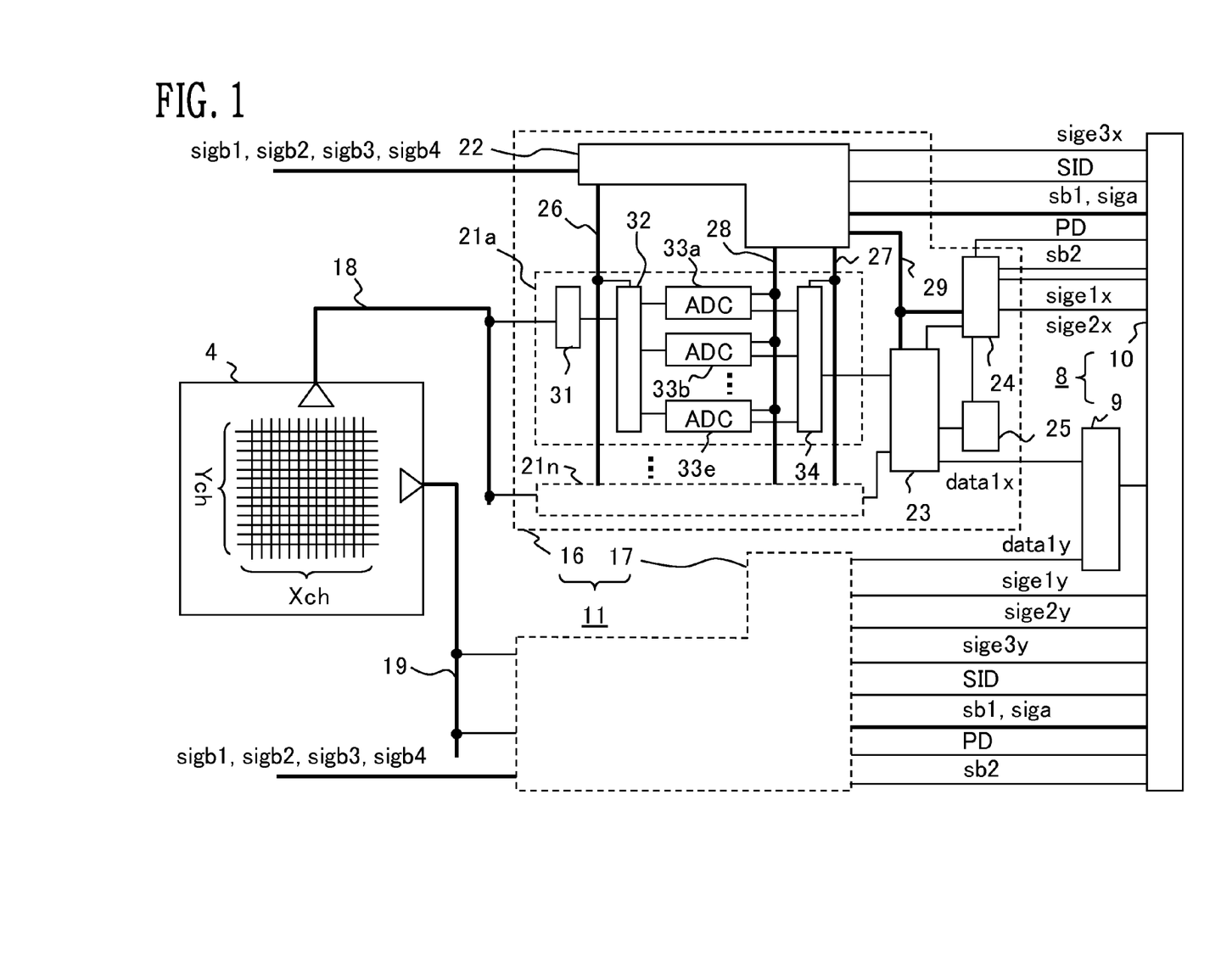
FIG. 1 is a diagram representing the configuration of a beam data processing apparatus according to Embodiment 1 of the present invention.
Figure 2:
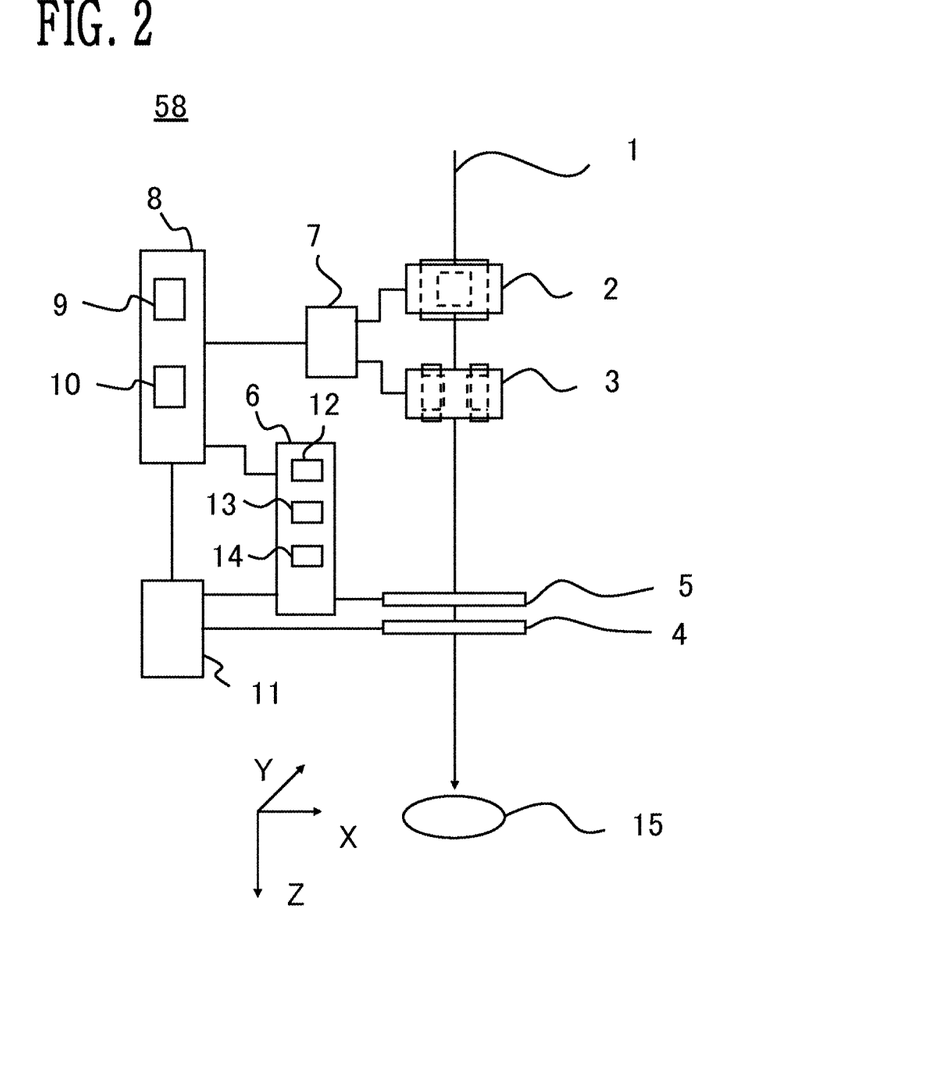
FIG. 2 is a diagram representing the configuration of a particle beam irradiation apparatus provided with the beam data processing apparatus in FIG. 1.
Figure 3:
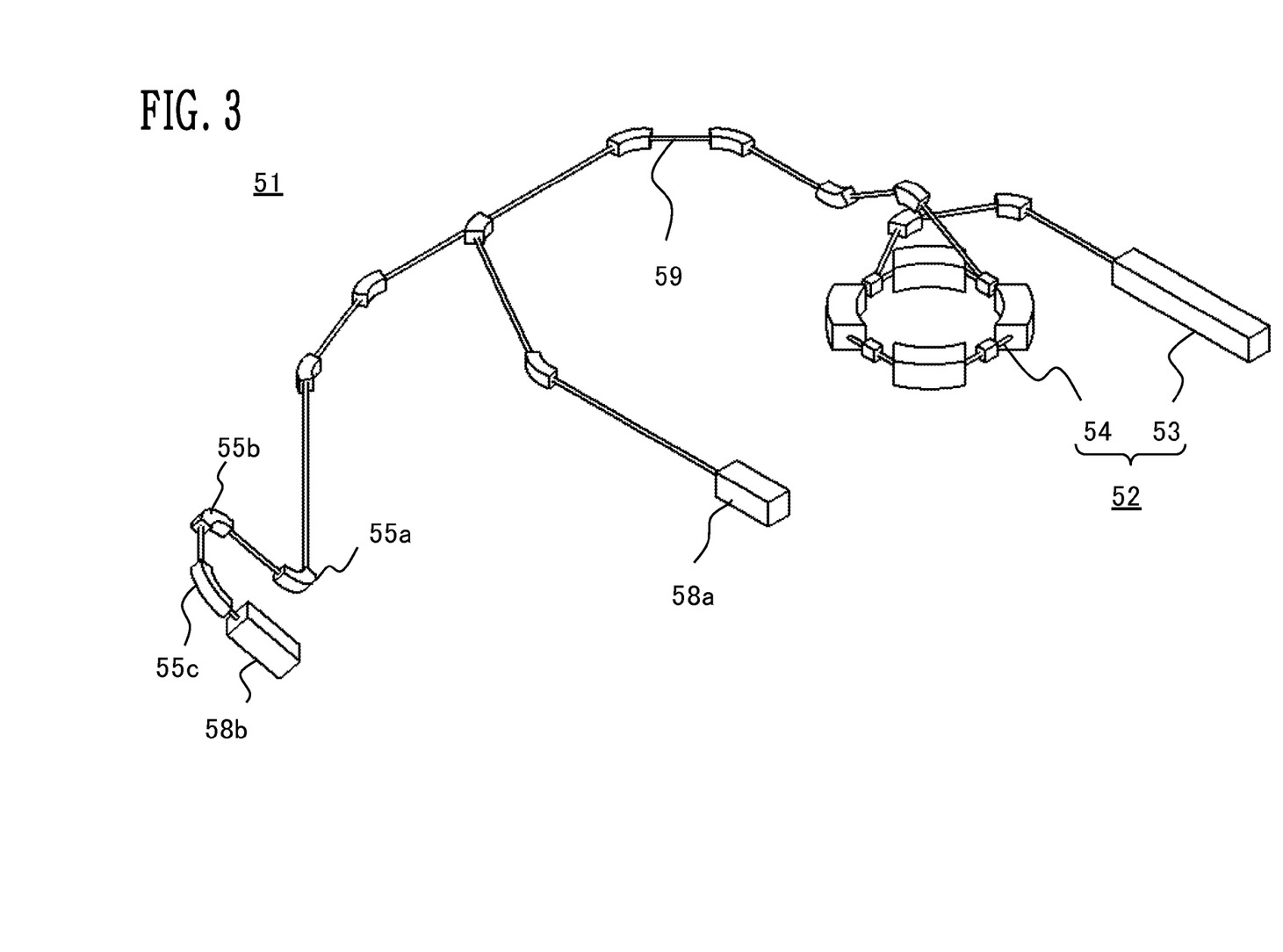
FIG. 3 is a schematic configuration diagram illustrating a particle beam therapy system according to Embodiment 1 of the present invention.

FIG. 1 is a diagram representing the configuration of a beam data processing apparatus according to Embodiment 1 of the present invention. FIG. 2 is a diagram illustrating the configuration of a particle beam irradiation apparatus provided with the beam data processing apparatus according to Embodiment 1 of the present invention; FIG. 3 is a schematic configuration diagram illustrating a particle beam therapy system according to Embodiment 1 of the present invention. In FIG. 3, a particle beam therapy system 51 includes a beam generation apparatus 52, a beam transport system 59, and particle beam irradiation apparatuses 58a and 58b. The beam generation apparatus 52 includes an ion source (unillustrated), a prestage accelerator 53, and a synchrotron 54. The particle beam irradiation apparatus 58b is provided in a rotating gantry (unillustrated). The particle beam irradiation apparatus 58a is provided in a treatment room where no rotating gantry is installed. The function of the beam transport system 59 is to achieve communication between the synchrotron 54 and the particle beam irradiation apparatuses 58a and 58b. Part of the beam transport system 59 is provided in the rotating gantry (unillustrated), and that part includes a plurality of deflection electromagnets 55a, 55b, and 55c.

A charged particle beam, which is a particle beam such as a proton beam generated in the ion source, is accelerated by the prestage accelerator 53 and enters the synchrotron 54, which is an accelerator. The particle beam is accelerated to gain predetermined energy. The charged particle beam launched from the synchrotron 54 is transported to the particle beam irradiation apparatuses 58a and 58b by way of the beam transport system 59. The particle beam irradiation apparatuses 58a and 58b each irradiate the charged particle beam onto an irradiation subject 15 (refer to FIG. 2).

A charged particle beam 1 generated in the beam generation apparatus 52 and accelerated to gain predetermined energy is led to the particle beam irradiation apparatus 58 by way of the beam transport system 59. In FIG. 2, the particle beam irradiation apparatus 58 is provided with X-direction and Y-direction scanning electromagnets 2 and 3 that scan the charged particle beam 1 in the X direction and the Y direction, respectively, which are directions perpendicular to the charged particle beam 1; a position monitor 4; a dose monitor 5; a dose data converter 6; a beam data processing apparatus 11; a scanning electromagnet power source 7; and an irradiation management apparatus 8 that controls the particle beam irradiation apparatus 58. The irradiation management apparatus 8 is provided with an irradiation control computer 9 and an irradiation control apparatus 10. The dose data converter 6 is provided with a trigger generation unit 12, a spot counter 13, and an inter-spot counter 14. The traveling direction of the charged particle beam 1 is the Z direction.

The X-direction and Y-direction scanning electromagnets 2 and 3 scan the charged particle beam 1 in the X direction and the Y direction, respectively. The position monitor 4 detects a beam passing position (gravity center position) and a beam size through which the charged particle beam 1 that has been scanned by the X-direction scanning electromagnet 2 and the Y-direction scanning electromagnet 3 passes. The dose monitor 5 detects the dose of the charged particle beam 1. The irradiation management apparatus 8 controls the irradiation position of the charged particle beam 1 on the irradiation subject 15, based on treatment plan data created by an unillustrated treatment planning apparatus; when the dose measured by the dose monitor 5 and converted into digital data by the dose data converter 6 reaches the desired dose, the charged particle beam 1 is stopped. The scanning electromagnet power source 7 changes setting currents for the X-direction scanning electromagnet 2 and the Y-direction scanning electromagnet 3, based on control inputs (commands), which are outputted from the irradiation management apparatus 8, to the X-direction scanning electromagnet 2 and the Y-direction scanning electromagnet 3.

In this Description, the scanning irradiation method for the particle beam irradiation apparatus 58 will be explained assuming that it is the raster-scanning irradiation method in which when the irradiation position of the charge particle beam 1 is changed, the charged particle beam 1 is not stopped, i.e., it is a method in which as is the case with the spot scanning irradiation method, the beam irradiation position travels through spot positions one after another. The spot counter 13 measures the irradiation dose for a time during which the beam irradiation position of the charged particle beam 1 is stopped. The inter-spot counter 14 measures the irradiation dose for a time during which the beam irradiation position of the charged particle beam 1 moves. The trigger generation unit 12 generates a starting signal with which the beam data processing apparatus obtains new data of the position monitor 4 while the beam irradiation position is stopped.

In FIG. 1, the beam data processing apparatus 11 includes an X data processing unit 16 that processes an X-channel signal of the position monitor 4 and a Y data processing unit 17 that processes a Y-channel signal of the position monitor 4. The X data processing unit 16 is connected with the position monitor 4 by way of an X-channel signal line 18; the Y data processing unit 17 is connected with the position monitor 4 by way of a Y-channel signal line 19. Each of the X-channel signal line 18 and the Y-channel signal line 19 includes signal lines, the number of which is the same as the number of a plurality of channel data conversion units 21. The respective configurations of the X data processing unit 16 and the Y data processing unit 17 are the same as each other. The X data processing unit 16 will be explained as an example. The X data processing unit 16 is provided with an integrated control unit 22, a position size processing unit 23, an abnormality determination processing unit 24, a data memory 25, and the plurality of channel data conversion units 21, the number of which coincides with the number of a plurality of X-channel signals of the position monitor 4. In FIG. 1, as far as the channel data conversion units 21 are concerned, only two of them are illustrated; the channel data conversion units between the two channel data conversion units 21a and 21n are omitted by providing a plurality of dots instead of them. Each of the X-channel signal line 18 and the Y-channel signal line 19 is illustrated with a single thick line in FIG. 1, for the purpose of preventing the drawing from becoming complex.

In the position monitor 4, a sensor unit is provided in the form of a mesh, and a great number of detection channels (channels in the X direction and channels in the Y direction) are provided. These many channels each output a current signal, as an analogue signal. The respective analogue signals of Xch (the X channel) of the position monitor 4 are connected with the channel data conversion units 21a through 21n, in the X data processing unit 16; the respective analogue signals of Ych (the Y channel) are connected with the channel data conversion units 21a through 21n, in the Y data processing unit 17. Xch corresponds to the X direction of the particle beam irradiation apparatus 58; Ych corresponds to the Y direction of the particle beam irradiation apparatus 58.

The channel data conversion unit 21a is provided with a current/voltage converter 31 that converts a current signal outputted from the position monitor 4 into a voltage signal, a demultiplexer 32 that distributes a voltage signal outputted from the current/voltage converter 31 to a plurality of A/D converters (analogue/digital converters) 33, a plurality of A/D converters 33, for example, five A/D converters 33a through 33e that perform A/D conversion processing in which the respective voltage signals distributed by the demultiplexer 32 are converted into digital signals, and a multiplexer 34 that switches and outputs the signals to which the A/D conversion processing has been applied in the plurality of A/D converters 33a through 33e. In FIG. 1, as far as the A/D converters 33 are concerned, only three of them are illustrated; the A/D converters between the two A/D converters 33b and 33e are omitted by providing a plurality of dots instead of them.

The integrated control unit 22 controls a plurality of channel data conversion units 21, the position size processing unit 23, and the abnormality determination processing unit 24. The respective channel data conversion units 21 are connected with the integrated control unit 22 by way of a demultiplexer switching signal line 26, a multiplexer switching signal line 27, and an A/D-related signal line 28. Each of the demultiplexer switching signal line 26 and the multiplexer switching signal line 27 includes signal lines, the number of which is the same as the number of a plurality of channel data conversion units 21. The A/D-related signal line 28 includes signal lines, the number of which is the same as the number of the A/D converters 33. A data ID signal line 29 (ID: identification) includes a spot ID data line and a sub-ID notification signal line. The integrated control unit 22, for example, receives a 25% dose completion signal sigb1, a 50% dose completion signal sigb2, a 75% dose completion signal sigb3, and a 100% dose completion signal sigb4, which are four starting signals with which the beam data processing apparatus 11 obtains new data of the position monitor 4. Each of the 25% dose completion signal sigb1, the 50% dose completion signal sigb2, the 75% dose completion signal sigb3, and the 100% dose completion signal sigb4 is a proportion dose completion signal that indicates that the dose of the charged particle beam 1 at an irradiation spot where the charged particle beam 1 is stopped has become a predetermined proportion of the desired dose. Each of the demultiplexer switching signal line 26, the multiplexer switching signal line 27, and the A/D-related signal line 28 is illustrated with a single thick line in FIG. 1, for the purpose of preventing the drawing from becoming complex. The position size processing unit 23 is connected with the integrated control unit 22 by way of the data ID signal line 29. In order to prevent the drawing from becoming complex, the data ID signal line 29 is expressed by a single thick line in FIG. 1. Each of the signal lines illustrated with a thick line is a signal line through which two or more kinds of signals are transmitted.

The position size processing unit 23 receives a voltage Vi that has been A/D-converted by the plurality of channel data conversion units 21, and calculates, based on the voltages Vi, a beam position P in such a manner as a gravity center is calculated. The position size processing unit 23 calculates a beam size S based on the voltages Vi, as if a standard deviation is calculated. The beam size S is a length corresponding to 1 σ of a one-dimensional Gaussian distribution. The position size processing unit 23 of the X data processing unit 16 calculates a beam position Px in the X direction and a beam size Sx; the position size processing unit 23 of the Y data processing unit 17 calculates a beam position Py in the Y direction and a beam size Sy. The position size processing unit 23 stores the calculated beam position P and beam size S in the data memory 25. The beam position Px and the beam size Sx are stored in the data memory 25 of the X data processing unit 16; the beam position Py and the beam size Sy are stored in the data memory 25 of the Y data processing unit 17.

Based on preset data PD received from the irradiation control apparatus 10 before the charged particle beam 1 is irradiated, the abnormality determination processing unit 24 determines whether or not there exists an abnormality in the beam position P or in the beam size S, i.e., whether or not the beam position P and the beam size S are allowable. When determining that the beam position P is not allowable, the abnormality determination processing unit 24 outputs a position abnormality signal sige1 to the irradiation control apparatus 10. When determining that the beam size S is not allowable, the abnormality determination processing unit 24 outputs a size abnormality signal sige2 to the irradiation control apparatus 10. The abnormality determination processing unit 24 of the X data processing unit 16 outputs a position abnormality signal sige1x and a size abnormality signal sige2x; the abnormality determination processing unit 24 of the Y data processing unit outputs a position abnormality signal sige1y and a size abnormality signal sige2y.

Each of the integrated control units 22 of the X data processing unit 16 and the Y data processing unit 17 receives a spot ID, an inter-spot travel completion signal siga, and a spot ID strobe sb1 from the irradiation control apparatus 10 and outputs an ADC processing abnormality signal sige3 to the irradiation control apparatus 10. SID in FIG. 1 denotes a spot ID. The integrated control unit 22 of the X data processing unit 16 outputs an ADC processing abnormality signal sige3x to the irradiation control apparatus 10; the integrated control unit 22 of the Y data processing unit 17 outputs an ADC processing abnormality signal sige3y to the irradiation control apparatus 10. The ADC processing abnormality signal sige3 is outputted when all of the A/D converters 33a through 33e of the channel data conversion unit 21 are processing. For example, in the case where each of the A/D converters 33a through 33e outputs an ADC processing starting signal sigd1 and no ADC processing ending signal sigd2, the ADC processing abnormality signal sige3 is outputted when the integrated control unit 22 receives trigger signals (siga, sigb1, sigb2, sigb3, and sigb4), which indicate that collection of the next data has been instructed. As the reference character for a spot ID, SID is utilized; however, in the case where a spot ID and the reference character SID are expressed in series, the spot ID is expressed as "spot identity SID" in order to prevent confusion between spot ID and reference character SID.

Each of the abnormality determination processing unit 24s of the X data processing unit 16 and the Y data processing unit receives the preset data PD and a preset value strobe sb2 from the irradiation control apparatus 10 and outputs the position abnormality signal sige1 and the size abnormality signal sige2 to the irradiation control apparatus 10.

After the irradiation of the charged particle beam 1 has been completed, the respective position size processing units 23 of the X data processing unit 16 and the Y data processing unit each output actual performance data data1 on the beam position P and the beam size S to the irradiation control computer 9. As described later, the actual performance data data1 includes information indicating a positional abnormality and a beam size abnormality. The position size processing unit 23 of the X data processing unit 16 outputs actual performance data data1x to the irradiation control computer 9; the position size processing unit 23 of the Y data processing unit 17 outputs actual performance data data1y to the irradiation control computer 9.

Even in the case where when the charged particle beam 1 is being irradiated at an irradiation spot, a positional abnormality or a size abnormality of the charged particle beam 1 is caused, the beam data processing apparatus 11 detects the beam position P, which is the irradiation position of the charged particle beam 1, and the beam size S of the charged particle beam 1; then, the beam data processing apparatus 11 generates an abnormality detection signal indicating a positional abnormality or a size abnormality of the charged particle beam 1. The position abnormality signal sige1 is an abnormality detection signal indicating a positional abnormality of the charged particle beam 1. The position abnormality signal sige2 is an abnormality detection signal indicating a size abnormality of the charged particle beam 1. The operation of the beam data processing apparatus 11 will be explained by use of a timing chart.

Figure 4:
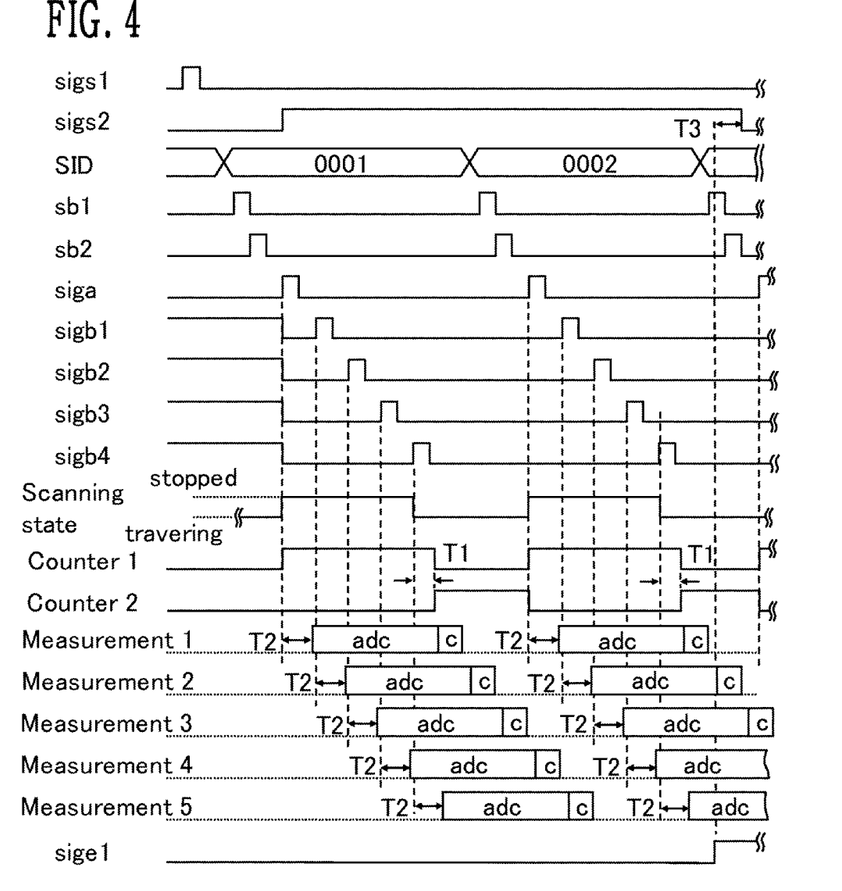
FIG. 4 is a timing chart for explaining the operation of the beam data processing apparatus in FIG. 1.
Figure 5:
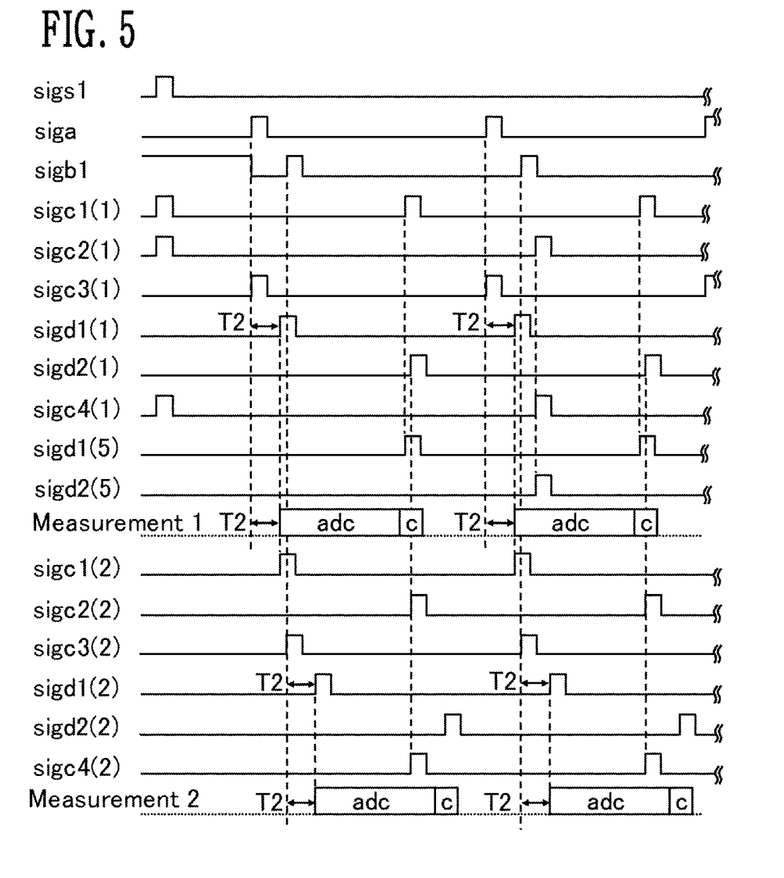
FIG. 5 is a timing chart for explaining the operation of an integrated control unit in FIG. 1.

FIG. 4 is a timing chart for explaining the operation of the beam data processing apparatus; FIG. 5 is a timing chart for explaining the operation of the integrated control unit. The timing chart in FIG. 4 represents an example in which data on the position monitor 4 is collected five times at a single irradiation spot and each time the data is collected, the beam position P and the beam size S are calculated based on the AD-converted data. Measurements 1 through 5 each represent the respective timings of AD conversion processing and calculation of the beam position P and the beam size S. A period designated by "adc" indicates the period of AD conversion processing; a period designated by "c" indicates the period of calculation of the beam position P and the beam size S. The trigger signals for starting the five A/D conversion processing actions, are, for example, the inter-spot travel completion signal siga, the 25% dose completion signal sigb1, the 50% dose completion signal sigb2, the 75% dose completion signal sigb3, and the 100% dose completion signal sigb4, as described above.

The irradiation control apparatus 10 of the irradiation management apparatus 8 transmits a scanning start command sigs1 to the respective apparatuses in the particle beam therapy system 51; then, the irradiation of the charged particle beam 1 is started. The irradiation control apparatus 10 transmits the spot identity SID, the spot ID strobe sb1, and the preset value strobe sb2 to the beam data processing apparatus 11. The integrated control unit 22 of the beam data processing apparatus 11 receives the spot identity SID at the rising timing of the spot ID strobe sb1. At the rising timing of the preset value strobe sb2, the abnormality determination processing unit 24 of the beam data processing apparatus 11 designates data corresponding to the spot identity SID, in the preset data PD, that has been preliminary received. The preset data PD includes a desired position Pd (Pdx, Pdy) and a position allowable value AP for performing abnormality determination on the beam position P (Px, Py) and a desired beam size Sd (Sdx, Sdy) and a size allowable value AS for performing abnormality determination on the beam size S (Sx, Sy).

The irradiation control apparatus 10 transmits a beam-on command sigs2 to the beam generation apparatus 52. The charged particle beam 1 is led from the beam generation apparatus 52 to the particle beam irradiation apparatus 58 by way of the beam transport system 59. The irradiation control apparatus 10 transmits to the beam data processing apparatus 11 the inter-spot travel completion signal siga indicating that setting of instructions, to the X-direction scanning electromagnet 2 and the Y-direction scanning electromagnet 3, that corresponds to the initial spot identity SID ("0001" in FIG. 4) has been completed. When the initial inter-spot travel completion signal siga is transmitted, the integrated control unit 22 switches the demultiplexers 32 so that data of the position monitor 4 is inputted to the first A/D converter 33a and switches the multiplexers 34 so that processing data of the first A/D converter 33a is outputted to the position size processing unit 23. As represented in Measurement 1, when a measurement delay time T2, which is a mode transition time in the monitor, has elapsed after the rising timing of the initial inter-spot travel completion signal siga, the first A/D converter 33a starts AD conversion processing.

When the dose of the charged particle beam 1 comes into the states of 25% dose completion, 50% dose completion, 75% dose completion, and 100% dose completion of the desired dose at the irradiation spot corresponding to the spot identity SID, the trigger generation unit 12 of the dose data converter 6 outputs the integrated control unit 22 the 25% dose completion signal sigb1, the 50% dose completion signal sigb2, the 75% dose completion signal sigb3, and the 100% dose completion signal sigb4, respectively.

When receiving the ADC processing starting signal sigd1 (refer to FIG. 5) for the first A/D converter 33a through an after-mentioned demultiplexer procedure, the integrated control unit 22 switches the demultiplexers 32 so that data of the position monitor 4 is inputted to the second A/D converter 33b. After that, when receiving the 25% dose completion signal sigb1, the integrated control unit 22 outputs the ADC processing starting command sigc3 to the second A/D converter 33b so as to make the second A/D converter 33b start AD conversion processing. As represented in Measurement 2, when the measurement delay time T2, which is the mode transition time in the monitor, has elapsed after the rising timing of the 25% dose completion signal sigb1, the second A/D converter 33b starts AD conversion processing. Similarly, when receiving the ADC processing starting signal sigd1 for the second A/D converter 33b, the ADC processing starting signal sigd1 for the third A/D converter 33c, and the ADC processing starting signal sigd1 for the fourth A/D converter 33d, the integrated control unit 22 sequentially switches the demultiplexers 32 so that data of the position monitor 4 is inputted to the third A/D converter 33c, the fourth A/D converter 33d, and the fifth A/D converter 33e, respectively. After the demultiplexer procedure has been completed, when receiving the 50% dose completion signal sigb2, the 75% dose completion signal sigb3, and the 100% dose completion signal sigb4, the integrated control unit 22 outputs the ADC processing starting command sigc3 to the third A/D converter 33c, the fourth A/D converter 33d, and the fifth A/D converter 33e, respectively. AS represented in Measurements 3 through 5, when the measurement delay time T2, which is the mode transition time in the monitor, has elapsed after each of the rising timings of the 50% dose completion signal sigb2, the 75% dose completion signal sigb3, and the 100% dose completion signal sigb4, the third A/D converter 33c, the fourth A/D converter 33d, and the fifth A/D converter 33e, respectively, start AD conversion processing. As described above, taking a particle that arrives in a delayed manner into consideration, the start of AD conversion processing is delayed.

The counters 1 and 2 in FIG. 4 represents the counting periods (dose measurement periods) of the spot counter 13 and the inter-spot counter 14, respectively. The upper side (state 1) of each waveform suggests that the counting is being performed, and the lower side (state 0) of each waveform suggests that the counting is stopped. The scanning state in FIG. 4 represents the state of scanning the charged particle beam 1. The upper side (state 1) of the scanning state suggests that the charged particle beam 1 is stopped at an irradiation spot, and the lower side (state 0) of the scanning state suggests that the charged particle beam 1 is traveling to the next irradiation spot. Even when the scanning of the charged particle beam 1 to the next irradiation spot has been started, the spot counter 13 continues the measurement until the spot delay time T1 elapses. The spot delay time T1 corresponds to a control delay before control of the X-direction scanning electromagnet 2 and the Y-direction scanning electromagnet 3 for the scanning to the next irradiation spot is started.

The integrated control unit 22 controls the demultiplexer 32 and the multiplexer 34, based on the ADC processing starting signal sigd1 and the ADC processing ending signal sigd2 (refer to FIG. 5) for each of the A/D converters 33a through 33e. That is to say, the integrated control unit 22 collects beam data (data of Measurement 1) at a time when the charged particle beam 1 has started to halt at an irradiation spot and beam data (data pieces of Measurements 2 through 5) at a time when the dose has reached a predetermined value, and controls the demultiplexer 32 and the multiplexer 34 so that the beam data is transmitted to the position size processing unit 23 (a data collection procedure). Then, based on the collected beam data, the position size processing unit 23 calculates the beam position P and the beam size S (a position size calculation procedure).

When the next spot identity SID ("0002" in FIG. 4) is transmitted from the irradiation control apparatus 10 to the beam data processing apparatus 11, the integrated control unit of the beam data processing apparatus 11 receives the spot identity SID at the rising timing of the spot ID strobe sb1 and repeats the foregoing data collection procedure and position size calculation procedure.

After receiving the beam position P and the beam size S from the position size processing unit 23, the abnormality determination processing unit 24 determines whether or not the beam position P and the beam size S are allowable, based on the preset data PD. For example, when determining, with regard to the result of the second calculation in Measurement 1, that the beam position P is not allowable, the abnormality determination processing unit 24 outputs the position abnormality signal sige1 to the irradiation control apparatus 10. The irradiation control apparatus 10 receives the position abnormality signal sige1 and then cancels the beam-on command sigs2 after an interlock operation time T3 has elapsed. In this situation, cancellation of the beam-on command sigs2 is equivalent to issuing a command of turning off the beam. In response to the cancellation of the beam-on signal sigs2, the beam generation apparatus 52 stops the generation of the charged particle beam 1.

With reference to FIG. 5, the operation of the integrated control unit 22 will be explained in detail. The integrated control unit 22 controls the demultiplexer 32, the A/D converter 33, and the multiplexer 34, by use of a demultiplexer switching command sigc1, a multiplexer switching command sigc2, the ADC processing starting command sigc3, the ADC processing starting signal sigd1, and the ADC processing ending signal sigd2. FIG. 5 represents an example in which in order to control the five A/D converters 33a through 33e, the demultiplexer switching command sigc1, the multiplexer switching command sigc2, the ADC processing starting command sigc3, a data ID signal sigc4, the ADC processing starting signal sigd1, and the ADC processing ending signal sigd2 are utilized. The respective numerals in parentheses added to signal names correspond to Measurements 1 through 5. The explanation will be made under the assumption that each of Measurements 1 through 5 is implemented by use of the A/D converters 33a through 33e.

When receiving the scanning start command sigs1 outputted from the irradiation control computer 9, the integrated control unit 22 outputs the demultiplexer switching command sigc1(1), the multiplexer switching command sigc2(1), and the data ID signal sigc4(1) so as to activate the first A/D converter 33a. When receiving the demultiplexer switching command sigc1(1), the demultiplexer 32 switches the transmission paths so that a signal outputted from the current/voltage converter 31 is transmitted to the A/D converter 33a. When receiving the multiplexer switching command sigc2(1), the multiplexer 34 switches the transmission paths so that data outputted from the A/D converter 33a is transmitted to the position size processing unit 23. When receiving the data ID signal digc4(1), which is a signal for notifying a spot identity SID and a sub-ID, the position size processing unit 23 and the abnormality determination processing unit 24 store the spot identity SID and the sub-ID of data transmitted from the current/voltage converter 31. In this situation, the sub-ID also indicates what number the present measurement is. For example, in the case where the measurement is implemented five times at a single irradiation spot, the sub-ID is from 1 to 5.

When receiving the inter-spot travel completion signal siga outputted from the irradiation control apparatus 10, the integrated control unit 22 outputs the ADC processing starting command sigc3(1) to the A/D converter 33a. When receiving the ADC processing starting command sigc3(1), the A/D converter 33a outputs the ADC processing starting signal sigd1(1) to the integrated control unit 22 after the measurement delay time T2 has elapsed and starts AD conversion processing.

When receiving the ADC processing starting signal sigd1(1) from the A/D converter 33a, the integrated control unit 22 outputs the demultiplexer switching command sigc1(2) to the demultiplexer 32. When receiving the demultiplexer switching command sigc1(2), the demultiplexer 32 switches the transmission paths so that a signal outputted from the current/voltage converter 31 is transmitted to the A/D converter 33b. When receiving the 25% dose completion signal sigb1 outputted from the dose data converter 6, the integrated control unit 22 outputs the ADC processing starting command sigc3(2) to the A/D converter 33b. When receiving the ADC processing starting command sigc3(2), the A/D converter 33b outputs the ADC processing starting signal sigd1(2) to the integrated control unit 22 after the measurement delay time T2 has elapsed and starts AD conversion processing.

With regard to the second and subsequent transmission-path switching actions by the demultiplexer 32, when receiving the ADC processing starting signal sigd1, which indicates that the A/D converter 33 corresponding to the immediately previous sub-ID has received the signal from the current/voltage converter 31 and then AD conversion processing has been started, the integrated control unit 22 outputs to the demultiplexer 32 the demultiplexer switching command sigc1 for switching the transmission paths so that the signal from the current/voltage converter 31 is transmitted to the A/D converter 33 corresponding to the next sub-ID (a demultiplexer switching procedure). Also in Measurements 3 through 5, the demultiplexer switching procedure is implemented in a similar manner as described above. In FIG. 5, when receiving the ADC processing starting signal sigd1(5), the integrated control unit 22 outputs to the demultiplexer 32 the demultiplexer switching command sigc1(1) for switching the transmission paths so that the signal from the current/voltage converter 31 is transmitted to the A/D converter 33a corresponding to the next sub-ID.

Next, a multiplexer switching procedure will be explained. After the AD conversion processing has been completed, the A/D converter 33a outputs the ADC processing ending signal sigd2(1) to the integrated control unit 22. When receiving the ADC processing ending signal sigd2(1), the integrated control unit outputs the multiplexer switching command sigc2(2) to the multiplexer 34 and outputs the data ID signal sigc4(1) to the position size processing unit 23 and the abnormality determination processing unit 24. When receiving the multiplexer switching command sigc2(2), the multiplexer 34 switches the transmission paths so that data outputted from the second A/D converter 33b is transmitted to the position size processing unit 23. When receiving the data ID signal digc4(2), the position size processing unit 23 and the abnormality determination processing unit 24 store the spot identity SID and the sub-ID that are transmitted next.

The multiplexer switching procedure will be summarized. When receiving the ADC processing ending signal sigd2, the integrated control unit 22 outputs the multiplexer switching command sigc2 corresponding to the next sub-ID to the multiplexer 34 and outputs the data ID signal sigc4 corresponding to the next sub-ID to the position size processing unit 23 and the abnormality determination processing unit 24. Also in Measurements 3 through 5, the demultiplexer switching procedure is implemented in a similar manner as described above.

Next, the operation at the irradiation spot corresponding to the second spot identity SID ("0002" in FIG. 4) will be explained. As described above, before the pulse of the second inter-spot travel completion signal siga is outputted from the irradiation control apparatus 10, when receiving the demultiplexer switching command sigc1(1) outputted from the integrated control unit 22, the demultiplexer 32 switches the transmission paths so that a signal outputted from the current/voltage converter 31 is transmitted to the A/D converter 33a. When receiving the inter-spot travel completion signal siga outputted from the irradiation control apparatus 10, the integrated control unit 22 outputs the ADC processing starting command sigc3(1) to the A/D converter 33a. When receiving the ADC processing starting command sigc3(1), the A/D converter 33a outputs the ADC processing starting signal sigd1(1) to the integrated control unit 22 after the measurement delay time T2 has elapsed and starts AD conversion processing. The operation thereafter is the same as the operation described above.

Figure 6:
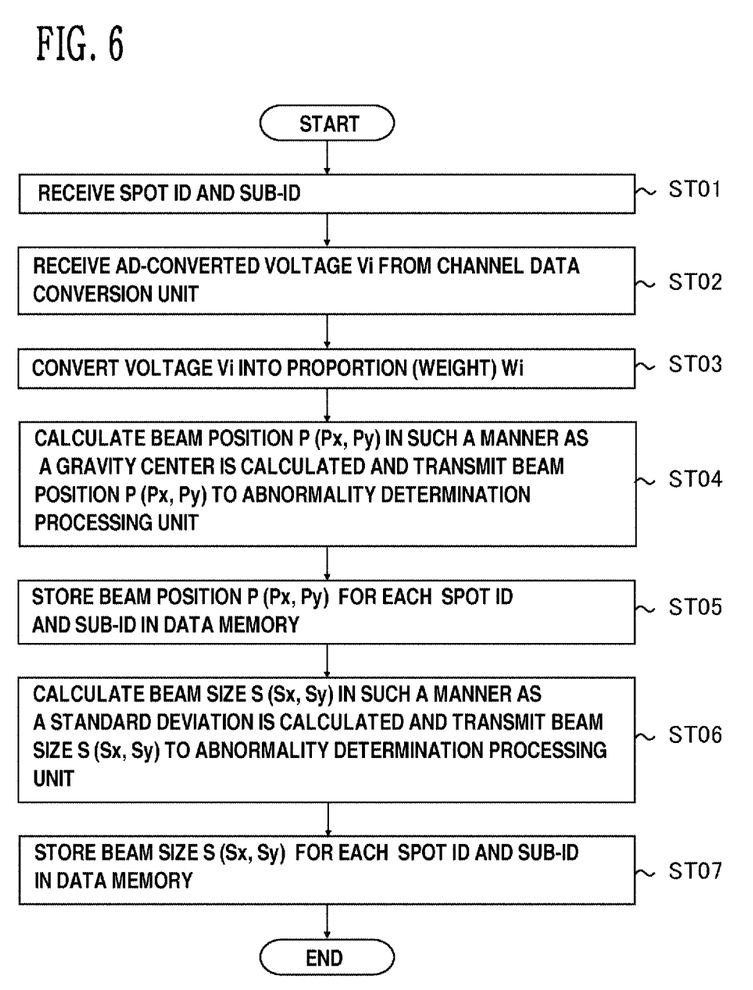
FIG. 6 is a flowchart for explaining the operation of a position size processing unit in FIG. 1.

The operation of the position size processing unit 23 will be explained by use of a flowchart. FIG. 6 is a flowchart for explaining the operation of the position size processing unit. In the step ST01, the position size processing unit 23 receives the spot identity SID and the sub-ID. In the step ST02, the position size processing unit 23 receives a voltage Vi, which has been AD-converted, from the channel data conversion unit 21. In the step ST03, the respective voltages Vi are converted into predetermined proportions wi. The proportion wi corresponds to the weight utilized when the beam position P is calculated in such a manner as a gravity center is calculated.

In the step ST04, the position size processing unit 23 calculates, through the equations (1) and (2) below, the beam position P (Px, Py) in such a manner as a gravity center is calculated. The position size processing unit 23 of the X data processing unit 16 calculates the beam position Px; the position size processing unit 23 of the Y data processing unit 17 calculates the beam position Py.

$$Px = \Sigma(wix \times Xi)/\Sigma wix \quad (1)$$

$$Py = \Sigma(wiy \times Yi)/\Sigma wiy \quad (2)$$

where Xi is the X coordinate of "i" in the X channel of the position monitor 4, and Yi is the Y coordinate of "i" in the Y channel of the position monitor 4; wix is the proportion obtained converting the voltage Vi of "i" in the X channel, and wiy is the proportion obtained converting the voltage Vi of "i" in the Y channel.

In the step ST04, after completion of the calculation of the beam position P (Px, Py), the position size processing unit transmits the calculated beam position P (Px, Py) to the abnormality determination processing unit 24. In the step ST05, the position size processing unit 23 stores the beam position P (Px, Py) for each spot identity SID and sub-ID in the data memory 25.

In the step ST06, the position size processing unit 23 calculates, through the equations (3) and (4) below, the beam size S (Sx, Sy) in such a manner as a standard deviation is calculated.

$$Sx=\text{sqr}(\Sigma wix \times (Xi-Px)^2)/\Sigma wix) \quad (3)$$

$$Sy=\text{sqr}(\Sigma wiy \times (Yi-Py)^2)/\Sigma wiy) \quad (4)$$

where sqr is a function for performing a root calculation, and n is the sum of calculation subjects in the X and Y channels.

In the step ST06, after completion of the calculation of the beam size S (Sx, Sy), the position size processing unit 23 transmits the calculated beam size S (Sx, Sy) to the abnormality determination processing unit 24. In the step ST07, the position size processing unit 23 stores the beam size S (Sx, Sy) for each spot identity SID and the sub-ID in the data memory 25.

Figure 7:
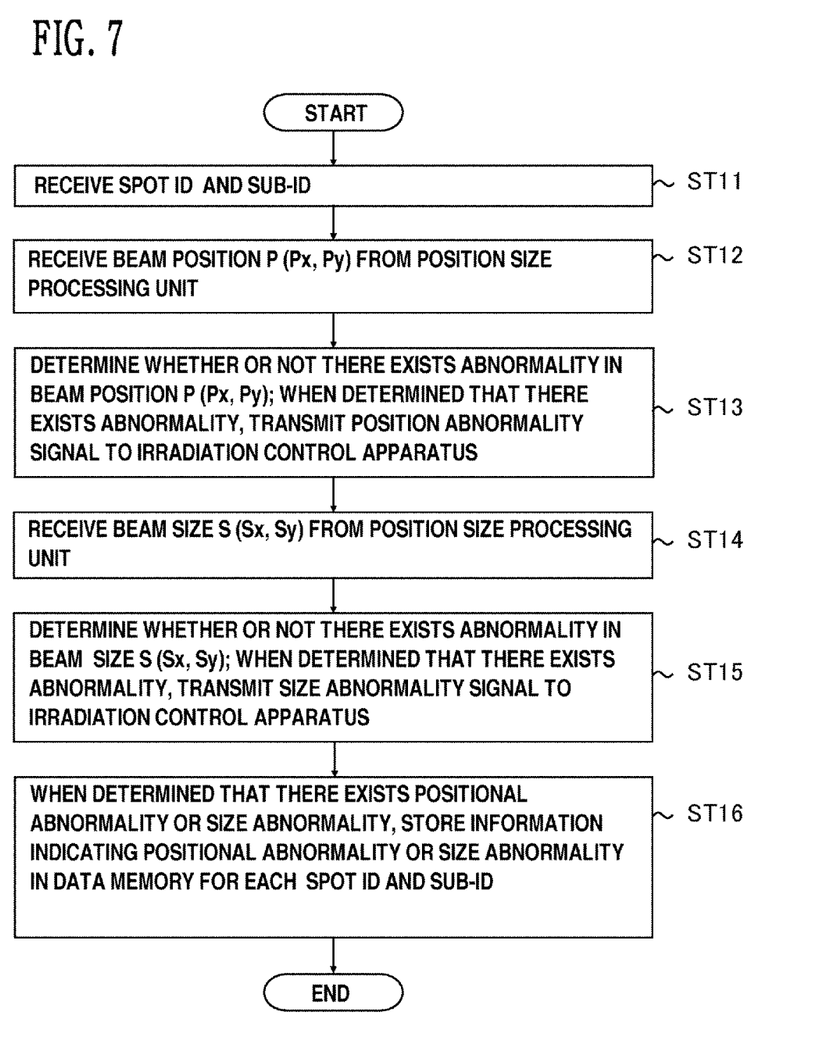
FIG. 7 is a flowchart for explaining the operation of an abnormality determination processing unit in FIG. 1.

The operation of the abnormality determination processing unit 24 will be explained by use of a flowchart. FIG. 7 is a flowchart for explaining the operation of the abnormality determination processing unit. In the step ST11, the abnormality determination processing unit 24 receives the spot identity SID and the sub-ID. In the step ST12, the abnormality determination processing unit 24 receives the beam position P (Px, Py) from the position size processing unit 23.

In the step ST13, the abnormality determination processing unit 24 determines whether or not there exists a positional abnormality. In other words, the abnormality determination processing unit 24 determines whether or not the absolute value of the difference ΔP between the beam position P (Px, Py) and the desired position Pd (Pdx, Pdy) is larger than the position allowable value AP. In the case where the absolute value of the difference ΔP is larger than the position allowable value AP, the abnormality determination processing unit 24 transmits the position abnormality signal sige1 to the irradiation control apparatus 10. The abnormality determination processing unit 24 of the X data processing unit 16 transmits the position abnormality signal sige1x to the irradiation control apparatus 10; the abnormality determination processing unit 24 of the Y data processing unit 17 transmits the position abnormality signal sige1y to the irradiation control apparatus 10.

In the step ST14, the abnormality determination processing unit 24 receives the beam size S (Sx, Sy) from the position size processing unit 23. In the step ST15, the abnormality determination processing unit 24 determines whether or not there exists a beam size abnormality. In other words, the abnormality determination processing unit 24 determines whether or not the absolute value of the difference ΔS between the beam size S (Sx, Sy) and the desired beam size Sd (Sdx, Sdy) is larger than the size allowable value AS. In the case where the absolute value of the difference AS is larger than the size allowable value AS, the abnormality determination processing unit 24 transmits the size abnormality signal sige2 to the irradiation control apparatus 10. The abnormality determination processing unit 24 of the X data processing unit 16 transmits the size abnormality signal sige2x to the irradiation control apparatus 10; the abnormality determination processing unit 24 of the Y data processing unit 17 transmits the size abnormality signal sige2y to the irradiation control apparatus 10.

In the step ST16, in the case where it is determined that there exists a positional abnormality or a beam size abnormality, the abnormality determination processing unit 24 stores in the data memory 25 information indicating that there exists a positional abnormality or a beam size abnormality, for each spot identity SID and sub-ID.

The beam data processing apparatus 11 according to Embodiment 1 can detect twice or more times the irradiation position P and the beam size S of the charged particle beam 1 while the charged particle beam 1 is stopped at an irradiation spot. Each time detecting the irradiation position P and the beam size S of the charged particle beam 1, the beam data processing apparatus 11 can determine whether or not there exists a positional abnormality or a size abnormality of the charged particle beam. Accordingly, the beam data processing apparatus 11 twice or more times detects the irradiation position P and the beam size S of the charged particle beam 1 while the charged particle beam 1 is stopped at an irradiation spot, and determines whether or not there exists a positional abnormality or a size abnormality of the charged particle beam each time the irradiation position P and the beam size S of the charged particle beam 1 are detected; therefore, even in the case where when the charged particle beam 1 is stopped at an irradiation spot and is being irradiated, a positional abnormality or a size abnormality is caused in the charged particle beam 1, it is made possible to determine that there exists the positional abnormality or the size abnormality of the charged particle beam 1.

When a positional abnormality or a size abnormality is caused in the charged particle beam 1, the beam data processing apparatus 11 transmits the position abnormality signal sige1 indicating the occurrence of the positional abnormality or the size abnormality signal sige2 indicating the occurrence of the size abnormality to the irradiation control apparatus 10 of the irradiation management apparatus 8. When receiving the trigger signal (siga, sigb1, sigb2, sigb3, or sigb4), which indicates that collection of the next data has been instructed, the beam data processing apparatus 11 transmits the ADC processing abnormality signal sige3 to the irradiation control apparatus 10 when all the A/D converters 33a through 33e of the channel data conversion unit 21 are performing processing (when AD conversion processing is being performed). In the case where while the charged particle beam 1 is irradiated, a positional abnormality, a size abnormality, or an AD conversion processing abnormality of the charged particle beam 1 is caused, the irradiation control apparatus 10 receives the position abnormality signal sige1, the size abnormality signal sige2, or the ADC processing abnormality signal sige3 from the beam data processing apparatus 11, so that interlock processing, which is emergency stop processing, can be implemented.

The beam data processing apparatus 11 according to Embodiment 1 is provided with two or more A/D converters 33 for each channel of the position monitor 4; therefore, the two or more A/D converters 33 can sequentially operate. Accordingly, even in the case where a single AD conversion processing takes a long time, data collection and AD conversion processing at a single irradiation spot can be implemented twice or more times. The beam data processing apparatus 11 can make two or more A/D converters 33 sequentially operate; therefore, unlike a beam data processing apparatus provided with only a single A/D converter 33 for each channel, the beam data processing apparatus 11 can start collection of data before on-going processing by the A/D converter 33 has been completed. Accordingly, it is not required to create a treatment plan restricted by the processing time of the A/D converter 33; thus, a treatment plan in which a single therapy irradiation ends in a shorter time is able to create. In other words, the therapy time can be shortened.

The particle beam irradiation apparatus 58 according to Embodiment 1 is provided with the beam data processing apparatus 11; therefore, in the case where while the charged particle beam is irradiated, a positional abnormality, a size abnormality, or an AD conversion processing abnormality of the charged particle beam 1 is caused, the particle beam irradiation apparatus 58 receives the position abnormality signal sige1, the size abnormality signal sige2, or the ADC processing abnormality signal sige3 from the beam data processing apparatus 11 so that interlock processing, which is emergency stop processing, can be implemented. Accordingly, in the case where a positional abnormality, a size abnormality, or AD conversion processing abnormality is caused in the charged particle beam 1, the particle beam irradiation apparatus 58 can stop the irradiation of the charged particle beam 1 in a short time.

The particle beam therapy system 51 according to Embodiment 1 is provided with the beam data processing apparatus 11; therefore, in the case where while the charged particle beam 1 is irradiated, a positional abnormality, a size abnormality, or an AD conversion processing abnormality of the charged particle beam 1 is caused, the particle beam therapy system 51 receives the position abnormality signal sige1, the size abnormality signal sige2, or the ADC processing abnormality signal sige3 from the beam data processing apparatus 11 so that interlock processing, which is emergency stop processing, can be implemented. Accordingly, in the case where a positional abnormality, a size abnormality, or AD conversion processing abnormality is caused in the charged particle beam 1, the particle beam therapy system 51 can stop the irradiation of the charged particle beam 1 in a short time.

As described above, the beam data processing apparatus 11 according to Embodiment 1 is provided with a plurality of channel data conversion units 21 that perform AD conversion processing in which each of the plurality of analogue signals outputted from the position monitor 4 that detects with a plurality of detection channels the passing position of the charged particle beam 1 is converted into a digital signal; the position size processing unit 23 that calculates the beam position P, which is the passing position of the charged particle beam 1 in the position monitor 4, based on voltage information items obtained through processing by the plurality of channel data conversion units 21; the abnormality determination processing unit 24 that determines whether or not the beam position P is within a tolerance range, based on the desired beam size Pd of the charged particle beam 1 and the position allowable value AP, and that generates the position abnormality signal sige1 when determining that the beam position P is not within the tolerance range; and the integrated control unit 22 that controls the plurality of channel data conversion units 21 in such a way that while the charged particle beam 1 is stopped at an irradiation spot, digital signal conversion processing is implemented two or more times. The channel data conversion unit 21 includes a plurality of A/D converters 33, the demultiplexer 32 that distributes respective analogue signals to the A/D converters 33 at different timings, and the multiplexer 34 that switches the respective digital signals processed by the A/D converters 33 at different timings so as to output them to the position size processing unit 23. As a result, a plurality of A/D converters 33 can be sequentially operated; therefore, it is made possible to detect the irradiation position P of the charged particle beam 1 even in the case where while the charged particle beam 1 is irradiated at an irradiation spot, a position abnormality of the charged particle beam 1 is caused and to generate an abnormality detection signal for indicating the position abnormality of the charged particle beam 1.

The particle beam therapy system 51 according to Embodiment 1 is provided with the beam generation apparatus 52 that generates the charged particle beam 1 and accelerates it by means of the accelerator 54, the beam transport system 59 that transports the charged particle beam 1 accelerated by the accelerator 54; and the particle beam irradiation apparatus 58 that irradiates the charged particle beam 1 transported by the beam transport system 59 onto the irradiation subject 15. The particle beam irradiation apparatus 58 has the scanning electromagnets 2 and 3 that scan the charged particle beam 1 to be irradiated onto the irradiation subject 15 and the beam data processing apparatus 11 that applies calculation processing to the state of the charged particle beam 1 that has been scanned by the scanning electromagnets 2 and 3. In the particle beam therapy system 51 according to Embodiment 1, the beam data processing apparatus 11 of the particle beam therapy system 51 is provided with a plurality of channel data conversion units 21 that perform AD conversion processing in which each of the plurality of analogue signals outputted from the position monitor 4 that detects with a plurality of detection channels the passing position of the charged particle beam 1 is converted into a digital signal; the position size processing unit 23 that calculates the beam position P, which is the passing position of the charged particle beam 1 in the position monitor 4, based on voltage information items obtained through processing by the plurality of channel data conversion units 21; the abnormality determination processing unit 24 that determines whether or not the beam position P is within a tolerance range, based on the desired beam size Pd of the charged particle beam 1 and the position allowable value AP, and that generates the position abnormality signal sige1 when determining that the beam position P is not within the tolerance range; and the integrated control unit 22 that controls the plurality of channel data conversion units 21 in such a way that while the charged particle beam 1 is stopped at an irradiation spot, digital signal conversion processing is implemented two or more times. The channel data conversion unit 21 includes a plurality of A/D converters 33, the demultiplexer 32 that distributes respective analogue signals to the A/D converters 33 at different timings, and the multiplexer 34 that switches the respective digital signals processed by the A/D converters 33 at different timings so as to output them to the position size processing unit 23. As a result, a plurality of A/D converters 33 can be sequentially operated; therefore, in the case where while the charged particle beam 1 is irradiated, a positional abnormality or a size abnormality of the charged particle beam 1 is caused, the position abnormality signal sige1 or the size abnormality signal sige2 is received from the beam data processing apparatus 11, so that interlock processing, which is emergency stop processing, can be implemented.

The difference ΔP between the beam position P (Px, Py) and the desired position Pd (Pdx, Pdy), which is calculated by the abnormality determination processing unit 24, can also be transmitted, as position feedback information, to the irradiation control apparatus 10. The irradiation control apparatus 10 may control the position of the charged particle beam 1, based on the position feedback information. Through the foregoing method, a positional deviation, which is not large enough to be determined as a positional abnormality, can be corrected.

In the flowchart in FIG. 6, an example has been explained in which the beam position P is calculated and then the beam size S is calculated; however, it may be allowed that two calculation units perform parallel processing of the beam position P and the beam size S. In this case, in the flowchart in FIG. 7, it may be allowed that data, out of the beam position P and the beam size S, that arrives earlier than the other is determined (position abnormality determination or size abnormality determination).

DESCRIPTION OF REFERENCE NUMERALS

1: charged particle beam
2: X-direction scanning electromagnet
3: Y-direction scanning electromagnet
4: position monitor
5: dose monitor
11: beam data processing apparatus
15: irradiation subject
21, 21a, 21n: channel data conversion unit
22: integrated control unit
23: position size processing unit
24: abnormality determination processing unit
32: demultiplexer
33, 33a, 33b, 33c, 33d, 33e: A/D converter
34: multiplexer
51: particle beam therapy system
52: beam generation apparatus
54: synchrotron
58, 58a, 58b: particle beam irradiation apparatus
59: beam transport system
P, Px, Py: beam position
Pd, Pdx, Pdy: desired position
AP: position allowable value
S, Sx, Sy: beam size
Sd, Sdx, Sdy: desired beam size
AS: size allowable value
siga: inter-spot travel completion signal
sigb1: 25% dose completion signal
sigb2: 50% dose completion signal
sigb3: 75% dose completion signal
sigb4: 100% dose completion signal
sigc3: ADC processing starting command
sigd1: ADC processing starting signal
sigd2: ADC processing ending signal
sige1: position abnormality signal
sige2: size abnormality signal

The invention claimed is:

1. A beam data processing apparatus that performs calculation processing of a state of a charged particle beam that has been accelerated by an accelerator and has been scanned by a scanning electromagnet in a particle beam therapy system for irradiating a diseased site, the beam data processing apparatus comprising:
a plurality of channel data conversion units that perform A/D conversion processing in which each of a plurality of analogue signals, outputted from a position monitor that detects the passing position of the charged particle beam within the position monitor, is converted into a digital signal;
an integrated control unit that controls the plurality of channel data conversion units;
wherein each of the channel data conversion units includes (i) a plurality of A/D converters that sequentially operate while the charged particle beam remains stationary to irradiate an irradiation spot of the diseased site, as controlled by the integrated control unit, such that one A/D converter begins A/D conversion processing prior to another A/D converter completing A/D conversion processing, (ii) a demultiplexer that distributes the respective analogue signals to the A/D converters at different timings while the charged particle beam remains stationary, and (iii) a multiplexer that switches the respective digital signals processed by the A/D converters at different timings, and
wherein said position monitor (i) is located at a downstream position with respect to said scanning electromagnet and (ii) includes a plurality of detection channels therein for detecting the passing position of the charged particle beam at the downstream location after having been scanned by said scanning electromagnet;
a position size processing unit that receives the digital signals output from the multiplexer and calculates a beam position, which is the passing position of the charged particle beam within the position monitor, based on voltage information items obtained through processing by the plurality of channel data conversion units; and
an abnormality determination processing unit (i) that determines whether or not the beam position within the position monitor is within a tolerance range, based on a desired position of the charged particle beam and a position allowable value, and (ii) that generates a position abnormality signal when determining that the beam position is not within the tolerance range.

2. The beam data processing apparatus according to claim 1, wherein the position size processing unit calculates a beam size of the charged particle beam that passes through the position monitor, based on voltage information items obtained through processing by the plurality of channel data conversion units; and the abnormality determination processing unit determines whether or not the beam size is within a tolerance range, based on a desired beam size of the charged particle beam and a size allowable value, and that generates a size abnormality signal when determining that the beam size is not within the tolerance range.

3. The beam data processing apparatus according to claim 1, wherein each time receiving an inter-spot travel completion signal indicating that setting of a command to the scanning electromagnet that scans the charged particle beam on the desired position has been completed and a proportion dose completion signal indicating that the dose of the charged particle beam at an irradiation spot where the charged particle beam is stationary has become a predetermined proportion of a desired dose, the integrated control unit outputs respective ADC processing starting commands to the different A/D converters so that the A/D conversion processing is started.

4. The beam data processing apparatus according to claim 1, wherein each time receiving an ADC processing starting signal indicating that one of the plurality of A/D converters has started the A/D conversion processing, the integrated control unit switches the transmission paths of the demultiplexer so that the analogue signal is transmitted to another one of the A/D converters that have not started the A/D conversion processing.

5. The beam data processing apparatus according to claim 1, wherein each time receiving an ADC processing ending signal indicating that one of the plurality of A/D converters has completed the A/D conversion processing, the integrated control unit switches the transmission paths of the multiplexer so that data from the A/D converter that is subsequently to end the A/D conversion processing is transmitted to the position size processing unit.

6. A particle beam therapy system comprising:
a beam generation apparatus that generates a charged particle beam and accelerates the charged particle beam by means of an accelerator;
a beam transport system that transports the charged particle beam accelerated by the accelerator; and
a particle beam irradiation apparatus that irradiates the charged particle beam transported by the beam transport system onto an irradiation subject, wherein the particle beam irradiation apparatus includes a scanning electromagnet that scans a charged particle beam to be irradiated onto the irradiation subject and a beam data processing apparatus that applies calculation processing to the state of a charged particle beam that has been scanned by the scanning electromagnet; and the beam data processing apparatus is the beam data processing apparatus according to claim 1.

* * * * *